United States Patent [19]

Nagi

[11] Patent Number: 5,985,325
[45] Date of Patent: Nov. 16, 1999

[54] RAPAMYCIN FORMULATIONS FOR ORAL ADMINISTRATION

[75] Inventor: Arwinder S. Nagi, Thiells, N.Y.

[73] Assignee: American Home Products Corporation, Madison, N.J.

[21] Appl. No.: 09/086,831

[22] Filed: May 29, 1998

Related U.S. Application Data

[60] Provisional application No. 60/050,954, Jun. 13, 1997.

[51] Int. Cl.$^6$ .......................... A61K 9/32; A61K 31/435; A61K 31/71
[52] U.S. Cl. .......................... 424/482; 424/122; 424/464; 424/474; 424/475; 424/479; 424/480
[58] Field of Search ...................................... 424/464, 465, 424/474, 475, 479, 480, 482, 490, 493, 497, 122

[56] References Cited

U.S. PATENT DOCUMENTS

| | | | |
|---|---|---|---|
| 3,929,992 | 12/1975 | Sehgal et al. | |
| 4,248,856 | 2/1981 | Guley et al. | 424/493 |
| 4,309,404 | 1/1982 | DeNeale et al. | 424/489 |
| 4,309,405 | 1/1982 | Guley et al. | 424/493 |
| 4,415,547 | 11/1983 | Yu et al. | 424/469 |
| 4,421,738 | 12/1983 | Yamagiwa et al. | 424/479 |
| 4,650,666 | 3/1987 | Izutsu et al. | 424/479 |
| 5,100,899 | 3/1992 | Calne. | |
| 5,352,783 | 10/1994 | Shafiee et al. | |
| 5,384,130 | 1/1995 | Kamada | 424/461 |
| 5,516,770 | 5/1996 | Waranis et al. | |
| 5,530,006 | 6/1996 | Waranis et al. | |
| 5,536,729 | 7/1996 | Waranis et al. | |
| 5,547,948 | 8/1996 | Barcomb | 514/170 |
| 5,559,121 | 9/1996 | Harrison et al. | |
| 5,616,588 | 4/1997 | Waranis et al. | |
| 5,759,576 | 6/1998 | Barcomb | 424/479 |
| 5,759,577 | 6/1998 | Barcomb | 424/479 |
| 5,766,623 | 6/1998 | Ayres et al. | 424/441 |

FOREIGN PATENT DOCUMENTS

| | | |
|---|---|---|
| 0525960 | 2/1993 | European Pat. Off. . |
| 0722720 | 7/1996 | European Pat. Off. . |

OTHER PUBLICATIONS

Derwent Assession No. 1987–318728.

*Primary Examiner*—Robert H. Harrison
*Attorney, Agent, or Firm*—Arnold S. Milowsky

[57] ABSTRACT

This invention provides rapamycin solid dosage unit which comprises a core and a sugar overcoat, said sugar overcoat comprising rapamycin, one or more sugars, and one or more binders.

9 Claims, No Drawings

RAPAMYCIN FORMULATIONS FOR ORAL ADMINISTRATION

This application claims the benefit of U.S. Provisional Application No. 60/050,954, filed Jun. 13, 1997.

This invention relates to formulations containing rapamycin, or pharmaceutically acceptable salts of rapamycin, which are useful in oral administrations for inducing immunosuppression and for treating transplantation rejection, host vs. graft disease, autoimmune diseases, diseases of inflammation, solid tumors, fungal infections, adult T-cell leukemia/lymphomas and hyperproliferative vascular disorders.

BACKGROUND OF THE INVENTION

Rapamycin is a macrolide antibiotic produced by *Streptomyces hygroscopicus* which was discovered first for its properties as an antifungal agent. It adversely affects the growth of fungi such as *Candida albicans* and *Microsporum gypseum*. Rapamycin, its preparation and its antibiotic activity were described in U.S. Pat. No. 3,929,992, issued Dec. 30, 1975 to Surendra Sehgal et al. In 1977 Martel, R. R. et al. reported on immunosuppressive properties of rapamycin against experimental allergic encephalitis and adjuvant arthritis in the Canadian Journal of Physiological Pharmacology, 55, 48–51 (1977). In 1989, Calne, R. Y. et al. in Lancet, 1989, no. 2, p. 227 and Morris, R. E. and Meiser, B. M. in Medicinal Science Research, 1989, No. 17, P. 609–10, separately reported on the effectiveness of rapamycin in inhibiting rejection in vivo in allograft transplantation. Numerous articles have followed describing the immunosuppressive and rejection inhibiting properties of rapamycin, and clinical investigations have begun for the use of rapamycin in inhibiting rejection in transplantation in man.

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The inmmunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., and Lancet 1183 (1978).

Rapamycin has been shown to inhibit transplantation rejection in mammals [U.S. Pat. No. 5,100,899]. Rapamycin, its derivatives and prodrugs have also been shown to be useful in treating pulmonary inflammation [U.S. Pat. No. 5,080,899], systemic lupus erythematosis [U.S. Pat. No. 5,078,899], immunoinflammatory skin disorders, such as psoriasis [U.S. Pat. No. 5,286,730], immunoinflammatory bowel disorders [U.S. Pat. No. 5,286,731], ocular inflammation [U.S. Pat. No. 5,387,589], hyperproliferative vascular disorders, such as restenosis [U.S. Pat. Nos. 5,512,781 and 5,288,711], carcinomas [U.S. Pat. No. 5,206,018 and 4,885,171], and cardiac inflammatory disease [U.S. Pat. No. 5,496,832]; and in preventing the onset of insulin dependent diabetes mellitus [U.S. Pat. No. 5,321,009]. Additionally, rapamycin has been shown to be useful in treating adult T-cell leukemia/lymphoma [European Pat. No. Application 525,960 A1], and in treating ocular inflammation [U.S. Pat. No. 5,387,589].

Because of its poor oil and water solubility, only a few formulations of rapamycin have proven satisfactory. U.S. Pat. Nos. 5,516,770 and 5,530,006 disclose intravenous rapamycin formulations, and U.S. Pat. Nos. 5,536,729 and 5,559,121 disclose liquid oral rapamycin formulations.

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions. U.S. Pat. No. 5,118,678 discloses carbamates of rapamycin that are useful as immunosuppressive, anti-inflammatory, antifungal, and antitumor agents. U. S. Pat. No. 5,100,883 discloses fluorinated esters of rapamycin. U. S. Pat. No. 5,118,677 discloses amide esters of rapamycin. U. S. Pat. No. 5,130,307 discloses aminoesters of rapamycin. U. S. Pat. No. 5,117,203 discloses sulfonates and sulfamates of rapamycin. U.S. Pat. No. 5,194,447 discloses sulfonylcarbamates of rapamycin.

The primary immunosuppressive agent presently used for inhibiting rejection in the allograft transplantation of organs in man is SANDIMMUNE (cyclosporine). Cyclosporine is a cyclic polypeptide consisting of 11 amino acids. The intravenous injectable formulation of SANDIMMUNE (IV) is a sterile ampoule containing, per ml, 50 mg of cyclosporine, 650 mg of Cremophor® EL and alcohol Ph Helv. (32.9% by volume) (under nitrogen). For administration this mixture is diluted further with 0.9% Sodium Chloride Injection or 5% Dextrose Injection before use. (*Physicians' Desk Reference*, 45th ed., 1991, pp. 1962–64, Medical Economics Company, Inc.) The macrolide molecule designated FK506, which has certain structural similarities to rapamycin, is also currently undergoing clinical investigation for inhibiting rejection in allograft organ transplantation in man. FK506 is isolated from *Streptomyces tsuskubaensis* and is described in U.S. Pat. No. 4,894,366 to Okuhara et al., issued Jan. 16, 1990 R. Venkataramanan et al., in Transplantation Proceedings, 22, No. 1, Suppl., 1 pp 52–56 (February 1990), report that the intravenous injectable formulation of FK506 is provided as a 10 mg/ml solution of FK506 in polyoxyethylated castor oil (HCO-60, a surfactant) and alcohol. The intravenous preparation must be diluted with saline or dextrose and administered as an infusion for 1 to 2 hours.

The *Physicians' Desk Reference* (45th ed., 1991, p. 2119, Medical Economics Company, Inc.) lists SANDIMMUNE (cyclosporine) as available in 25 mg and 100 mg strength capsules and as an oral solution in 50 ml bottles. The 25 mg capsules contain 25 mg cyclosporine, USP, and alcohol, USP dehydrated, at a maximum of 12.7% by volume. The 100 mg capsules contain cyclosporine, USP, 100 mg and alcohol, USP dehydrated, at a maximum 12.7% by volume. Inactive ingredients in the oral capsules are corn oil, gelatin, glycerol, Labrafil M 2125 CS (polyoxyethylated glycolysed glycerides), red iron oxide, sorbitol, titanium dioxide, and other ingredients. The oral solution is available in 50 mg bottles containing cyclosporine, USP, 100 mg and Ph. Helv. alcohol at 12.5% by volume dissolved in olive oil, Ph. Helv./Labrafil M 1944 CS (polyoxyethylated oleic glycerides) vehicle which must be diluted further with milk, chocolate milk or orange juice before oral administration.

IMURAN (azathioprine, available from Burroughs Wellcome Co., Research Triangle Park, N.C.) is another orally administered immunosuppressive agent prescribed alone or in conjunction with other immunosuppressive agents. The *Physicians' Desk Reference* (45th ed., 1991, pp. 785–787, Medical Economics Company, Inc.) lists azathioprine as 6-[1-methyl-4-nitroimidazol-5-yl)thio]purine, which is provided for oral administration in scored tablets containing 50 mg azathioprine and the inactive ingredients lactose, magnesium stearate, potato starch, povidone, and stearic acid.

DESCRIPTION OF THE INVENTION

Methods of drug delivery are designed to deliver an acceptable dosage of the medication to the patient. In the case of oral formulations, it is highly desirable to provide a dosage form which meets this criteria and which can be effectively administered, preferably self-administered, in either clinical or non-clinical situations.

The present invention concerns formulations useful in the oral administration of rapamycin. Rapamycin has been shown to possess immunosuppressive, antirejection, antifungal and antiinflammatory activity in vivo and to inhibit thymocyte proliferation in vitro. Therefore, these formulations are useful in the treatment or inhibition of transplantation rejection such as kidney, heart, liver, lung, bone marrow, pancreas (islet cells), cornea, small bowel, and skin allografts, and heart valve xenografts; in the treatment or inhibition of graft vs. host disease; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like), and eye uveitis.

Rapamycin has also been shown to have antitumor, antifungal, and antiproliferative activities. The formulations of this invention therefore also useful in treating solid tumors, including sarcomas and carcinomas, such as astrocytomas, prostate cancer, breast cancer, small cell lung cancer, and ovarian cancer; adult T-cell leukemia/lymphoma; fungal infections; and hyperproliferative vascular diseases such as restenosis and atherosclerosis.

The present invention, also provides formulations for use in inducing immunosuppression in a mammal in such need.

In general, the formulations of this invention provides an oral tablet dosage form of rapamycin comprising a core which is overcoated with rapamycin, and a sugar coat containing one or more sugars and one or more binders. It is preferred that such dosage tablets contain 0.05–20 mg rapamycin, with it being more preferred that such tablet will contain 0.5–10 mg rapamycin.

The sugar used in the production of the sugar overcoat described in this invention is a sugar product, such as sucrose, derived from beet or cane sources or starch, saccharide, or polysaccharide converted sources, which are considered suitable for preparing the sugar overcoat. When used in preparing the solid dosage form of this invention, it is preferred that the sugar is sucrose.

When binders are used in preparing the rapamycin oral dosage tablets, these can include gum acacia, tragacanth, stearic acid, gelatin, casein, lecithin (phosphatides), carboxymethylcellulose calcium, carboxymethylcellulose sodium, methylcellulose, hydroxyethylcellulose, hydroxypropylcellulose, hydroxypropylmethycellulose phthalate, methyacrylate, microcrystalline cellulose, noncrystalline cellulose, polyvinylpyrrolidone (povidone, PVP), cetostearyl alcohol, cetyl alcohol, cetyl esters wax, dextrates, dextrin, lactose, dextrose, glyceryl monooleate, glyceryl monostearate, glyceryl palmitostearate, polyoxyethylene alkyl ethers, polyethylene glycols, polyoxyethylene castor oil derivatives, polyoxyethylene stearates, polyvinyl alcohol, and sorbitan fatty acid esters.

The dosage tablets described herein provide rapamycin contained in a sugar overcoat that has been overcoated onto a core. The core can either be pharmaceutically inert or can contain a pharmaceutically active agent. As used in describing this invention the term "sugar overcoat" refers to the rapamycin, sugar, and binder which coat the core.

The following provides a preferred formulation for the sugar overcoat of a solid dosage tablet containing 0.05–20 mg rapamycin.

a) rapamycin in an amount from about 0.05–20 mg
b) sucrose in a range from about 50–99% weight of the sugar overcoat
c) one or more binders in a range from about 0.1–10% weight of the sugar overcoat In the formulations described in this invention, the quantities of the ingredients specified as percentages will vary according to the weight of the sugar overcoat. The sugar overcoat described in this invention will typically weigh about 50–200 mg. Therefore in the above formulation, the quantity of sucrose would be about 25 mg (about 50% weight of the sugar overcoat) for a 50 mg sugar overcoat containing 20 mg rapamycin and 10% (5 mg) binders. Similarly, the percent weight of sucrose in the sugar overcoat can comprise greater than 99% of the sugar overcoat when a 200 mg sugar overcoat contains 0.05 mg rapamycin and 0.1% (0.2 mg) binders.

The following provides a more preferred formulation for the sugar overcoat of a solid dosage tablet containing 0.05–20 mg rapamycin, in which the sugar overcoat contains povidone and microcrystalline cellulose as binders.

a) rapamycin in an amount from about 0.05–20 mg
b) sucrose in a range from about 50–99% weight of the final overcoat
c) povidone in a range from about 0.2–1.0 % weight of the final overcoat
d) microcyrstalline cellulose in a range from about 0.1–3.0 % weight of the final overcoat A rapamycin containing oral dosage tablet containing the above constituents can be prepared according to the following procedure. In preparing the above formulation, about 40–60 mg water is used in preparing a 100 mg sugar overcoat; the water is subsequently removed during processing. Briefly, rapamycin is either milled using conventional milling techniques, for example with a Fitz or ball mill, or is micronized using conventional micronizing techniques, for example with a Trost or jet mill. Milled rapamycin typically has a 10–400 micron particle size, and micronized rapamycin typically has a 0.5–10 micron particle size. The required quantity of water is heated to around 65–70° C. and sucrose is added, and mixed well until the sucrose is dissolved. The solution is cooled to about 30–40° C. Povidone is added and mixed vigorously until dissolved. Rapamycin is added to the mixture and mixed well to uniformly disperse the rapamycin, Microcrystaline cellulose is added, and the mixture stirred to provide a uniform suspension. Additional water is added if necessary and the suspension is continuously mixed during the coating process. The mixture is spray coated onto a core in small portions, and air dried in between portions, until the desired tablet strength is formed. During the manufacturing process, the majority of the water is removed, such that approximately less than 5% water remains in each tablet. Typically less than 2% residual water is present in each tablet. The rapamycin containing oral dosage tablets can be optionally coated with a color coat followed by a polish coat if desirable. The color coat typically contains a sugar such as sucrose, and a pigment such as titanium dioxide, and the polish coat contains carnuba wax, which can be applied as a dispersion in a solvent, such as mineral spirits.

When the core is a pharmaceutically inert core, it is typically a placebo core which may contain lactose, microcrystalline cellulose, PEG-6000, and other binders and fillers. The core, can be sealed with shellac to prevent disintegration from occurring during the overcoating process. A sucrose coat may also be placed on top of the shellac coat prior to the overcoating process.

The sugar overcoating described in this invention can be prepared to typically weigh about 50–200 mg. Using the process described herein, a 100 mg sugar overcoat containing 0.05–20 mg rapamycin would be made from the following ingredients according to the procedure described above:

a) rapamycin in an amount from about 0.05–20 mg
c) sucrose in an amount from about 50–99 mg
d) povidone in an the amount from about 0.2–1.0 mg
e) microcyrstalline cellulose in an amount from about 0.1–3.0 mg
f) water in an amount from 40–60 mg (mostly removed during processing)

It is contemplated that when the formulations of this invention are used as an immunosuppressive or antiinflammatory agent, they can be administered in conjunction with one or more other immunoregulatory agents. Such other antirejection chemotherapeutic agents include, but are not limited to azathioprine, corticosteroids, such as prednisone and methylprednisolone, cyclophosphamide, cyclosporin A, FK-506, OKT-3, and ATG. By combining one or more of the formulations of the present invention with such other drugs or agents for inducing immunosuppression or treating inflammatory conditions, lesser amounts of each of the agents may be required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

The dosage requirements may vary the severity of the symptoms presented and the particular subject being treated. Projected daily oral dosages of rapamycin would be 0.05–25 mg, with preferred projected daily doses being 0.5–10 mg when rapamycin is used in combination therapy, and 1–25 mg when rapamycin is used as monotherapy. More preferred projected daily doses are 2–5 mg when rapamycin is used in combination therapy, and 5–15 mg when rapamycin is used as monotherapy.

Treatment will generally be initiated with small dosages less than the optimum dose of the compound. Thereafter the dosage is increased until the optimum effect under the circumstances is reached. Precise dosages will be determined by the administering physician based on experience with the individual subject treated. In general, the formulations of this invention are most desirably administered at a concentration that will generally afford effective results without causing any harmful or deleterious side effects.

The oral dosage tablet formulation of this invention can also be used to make oral dosage tablets containing derivatives of rapamycin, including, but not limited to rapamycin esters, carbamates, sulfates, ethers, oximes, carbonates, the like which are all well described in the patent literature.

The following provide the preparation and evaluation of representative examples of rapamycin solid dosage tablets.

EXAMPLE 1

The following shows the preparation and evaluation of a 3.0 mg rapamycin oral dosage tablet containing a 100 mg sugar overcoat.

Formula:

| Ingredients* | Amount |
| --- | --- |
| Rapamycin | 3.06 mg |
| Sucrose | 97.41 mg |
| Povidone | 0.510 mg |
| Microcrystaline cellulose | 1.020 mg |
| Water | 54.92 mg |

*A 2% overage is included in these quantities to account for manufacturing losses.

Manufacturing Directions

1. The water was heated to around 65–70° C., and sucrose was added and mixed well until dissolved. The solution was cooled to about 30–40° C.
2. Povidone was added and mixed vigorously until dissolved.
3. Milled or micronized rapamycin was added to the mixture and mixed well to uniformly disperse the rapamycin.
4. Microcrystaline cellulose was added, and the mixture stirred to provide a uniform suspension.
5. The resulting solution was spray coated onto a pharmaceutically inert core portionwise and air dried in between portions.

Evaluation

Six Cynomolgus monkeys, listed below as A–C, were administered the above formulation at a dose of 3 mg rapamycin per monkey and the following serum concentrations of rapamycin were determined at the indicated time after dosing.

| | Rapamycin Concentration (nanogram/ml)/Monkey Number | | |
| --- | --- | --- | --- |
| Time | A | B | C |
| 0 hr. | 0.00 | 0.00 | 0.00 |
| 0.25 hr. | 4.53 | 0.00 | 1.01 |
| 0.5 hr. | 7.85 | 0.49 | 2.26 |
| 1.0 hr. | 8.43 | 1.12 | 4.02 |
| 2 hr. | 4.51 | 1.58 | 4.34 |
| 4 hr. | 3.94 | 2.68 | 2.76 |
| 8 hr. | 6.50 | 5.33 | 6.67 |
| 12 hr. | 6.01 | 3.88 | 5.25 |
| 16 hr. | 5.31 | 3.69 | 5.04 |
| 24 hr. | 3.94 | 3.40 | 4.96 |

The results obtained demonstrate that serum concentrations of rapamycin were observed following the administration of a representative oral dosage tablet of this invention.

EXAMPLE 2

A 0.5 mg rapamycin oral dosage tablet containing a 100 mg sugar overcoat was prepared according the procedure described in Example 1. The following lists the quantities of ingredients used.

| Formula: | |
|---|---|
| Ingredients* | Amount |
| Rapamycin | 0.510 mg |
| Sucrose | 99.96 mg |
| Povidone | 0.510 mg |
| Microcrystaline cellulose | 1.020 mg |
| Water | 54.92 mg |

*A 2% overage is included in these quantities to account for manufacturing losses.

EXAMPLE 3

A 1.0 mg rapamycin oral dosage tablet containing a 100 mg sugar overcoat was prepared according the procedure described in Example 1. The following lists the quantities of ingredients used.

| Formula: | |
|---|---|
| Ingredients* | Amount |
| Rapamycin | 1.02 mg |
| Sucrose | 99.45 mg |
| Povidone | 0.510 mg |
| Microcrystaline cellulose | 1.020 mg |
| Water | 54.92 mg |

*A 2% overage is included in these quantities to account for manufacturing losses.

EXAMPLE 4

A 5.0 mg rapamycin oral dosage table containing a 100 mg sugar overcoat was prepared according the procedure described in Example 1. The following lists the quantities of ingredients used.

| Formula: | |
|---|---|
| Ingredients* | Amount |
| Rapamycin | 5.10 mg |
| Sucrose | 95.37 mg |
| Povidone | 0.510 mg |
| Microcrystaline cellulose | 1.020 mg |
| Water | 54.92 mg |

*A 2% overage is included in these quantities to account for manufacturing losses.

EXAMPLE 5

A 7.5 mg rapamycin oral dosage tablet containing a 100 mg sugar overcoat was prepared according the procedure described in Example 1. The following lists the quantities of ingredients used.

| Formula: | |
|---|---|
| Ingredients* | Amount |
| Rapamycin | 7.65 mg |
| Sucrose | 92.82 mg |
| Povidone | 0.510 mg |
| Microcrystaline cellulose | 1.020 mg |
| Water | 54.92 mg |

*A 2% overage is included in these quantities to account for manufacturing losses.

EXAMPLE 6

A 10 mg rapamycin oral dosage tablet containing a 100 mg sugar overcoat was prepared according the procedure described in Example 1. The following lists the quantities of ingredients used.

| Formula: | |
|---|---|
| Ingredients* | Amount |
| Rapamycin | 10.2 mg |
| Sucrose | 90.27 mg |
| Povidone | 0.510 mg |
| Microcrystaline cellulose | 1.020 mg |
| Water | 54.92 mg |

*A 2% overage is included in these quantities to account for manufacturing losses.

What is claimed:

1. A rapamycin solid dosage unit which comprises a tablet core and a sugar overcoat; said sugar overcoat comprises
    a) rapamycin in an amount from about 0.05–20 mg
    b) sucrose in a range from about 50–99% weight of the sugar overcoat
    c) povidone in a range from about 0.2–1.0% weight of the sugar overcoat, and
    d) microcrystalline cellulose in a range from about 0.1–3.0% weight of the sugar overcoat.

2. The dosage unit according to claim 1, wherein the povidone is contained as about 0.5% weight of said sugarcoat.

3. The dosage unit according to claim 2, wherein the microcrystalline cellulose as about 1% weight of said sugarcoat.

4. The dosage unit according to claim 1, wherein
    (a) rapamycin is contained in an amount of about 0.5 mg,
    (b) sucrose is contained in a range from about 95–99% weight of said sugar overcoat
    (c) povidone is contained as about 0.5% weight of said sugar overcoat, and
    (d) microcrystalline cellulose is contained as about 1% weight of said sugar overcoat.

5. The dosage unit according to claim 1, wherein
    (a) rapamycin is contained in an amount of about 1 mg,
    (b) sucrose is contained in a range from about 94–99% weight of said sugar overcoat
    (c) povidone is contained as about 0.5% weight of said sugar overcoat, and
    (d) microcrystalline cellulose is contained as about 1% weight of said sugar overcoat.

6. The dosage unit according to claim 1, wherein
    (a) rapamycin is contained in an amount of about 3 mg,
    (b) sucrose is contained in a range from about 90–99% weight of said sugar overcoat
    (c) povidone is contained as about 0.5% weight of said sugar overcoat, and (d) microcrystalline cellulose is contained as about 1% weight of said sugar overcoat.

7. The dosage unit according to claim 1, wherein
(a) rapamycin is contained in an amount of about 5 mg,
(b) sucrose is contained in a range from about 85–98% weight of said sugar overcoat
(c) povidone is contained as about 0.5% weight of said sugar overcoat, and
(d) microcrystalline cellulose is contained as about 1% weight of said sugar overcoat.

8. The dosage unit according to claim 1, wherein
(a) rapamycin is contained in an amount of about 7.5 mg,
(b) sucrose is contained in a range from about 80–97% weight of said sugar overcoat
(c) povidone is contained as about 0.5% weight of said sugar overcoat, and
(d) microcrystalline cellulose is contained as about 1% weight of said sugar overcoat.

9. The dosage unit according to claim 1, wherein
(a) rapamycin is contained in an amount of about 10 mg,
(b) sucrose is contained in a range from about 75–96% weight of said sugar overcoat
(c) povidone is contained as about 0.5% weight of said sugar overcoat, and
(d) microcrystalline cellulose is contained as about 1% weight of said sugar overcoat.

* * * * *